United States Patent [19]

Murib

[11] 4,420,620

[45] Dec. 13, 1983

[54] PREPARATION OF 2-PYRROLIDONES

[75] Inventor: Jawad H. Murib, Cincinnati, Ohio

[73] Assignee: National Distillers and Chemical Corporation, New York, N.Y.

[21] Appl. No.: 325,449

[22] Filed: Nov. 27, 1981

[51] Int. Cl.³ .......................................... C07D 201/08
[52] U.S. Cl. .................................................. 548/554
[58] Field of Search ............... 260/326.5 FN; 548/554

[56] References Cited

U.S. PATENT DOCUMENTS 2,976,805  7/1960  Kleinschmidt et al. ... 260/326.5 FN
3,103,509  9/1963  von Schickh ............. 260/326.5 FN
3,231,576  1/1966  Falbe et al. ............... 260/326.5 FN Primary Examiner—Nicholas S. Rizzo
Assistant Examiner—D. B. Springer
Attorney, Agent, or Firm—Kenneth D. Tremain

[57] ABSTRACT 2-pyrrolidone and N-substituted 2-pyrrolidones such as N-methyl 2-pyrrolidone and N-(beta-hydroxyethyl)-2-pyrrolidone are prepared by the catalyzed reaction of methyl 4-oxobutyrate with ammonia or a primary amine and hydrogen.

7 Claims, No Drawings

PREPARATION OF 2-PYRROLIDONES

BACKGROUND OF THE INVENTION

This invention relates to the manufacture of pyrrolidones (or lactams) such as 2-pyrrolidone, N-methyl-2-pyrrolidone and N-(beta-hydroxyethyl)-2-pyrrolidone, the latter being capable of undergoing catalytic dehydration to provide N-vinyl-2-pyrrolidone.

2-Pyrrolidone and its N-substituted derivatives have achieved considerable commercial importance, notably as solvents and monomers, and a variety of synthetic procedures have been proposed for their manufacture. U.S. Pat. No. 2,267,757 to Schuster describes a process for obtaining N-alkyl, cycloalkyl, aralkyl or aryl pyrrolidones by reacting gamma-butyrolactone with primary amines at elevated temperature in the presence of catalysts splitting off water. U.S. Pat. No. 2,351,939 to Drossbach, et al. discloses the production of lactams by passing a vaporized dicarboxylic acid of at least four, and preferably six, carbon atoms with ammonia and hydrogen over catalysts having a hydrogenating and dehydrating action, e.g., conventional hydrogenation catalysts such as nickel, cobalt and copper and conventional dehydration catalysts such as phosphoric acid and boric acid. U.S. Pat. No. 2,669,570 to Schnizer discloses that N-vinylpyrrolidone is obtained by reacting ethanolamine with gamma butyrolactone to form N-beta-hydroxyethyl-gamma-hydroxybutyramide and then subjecting the amide to dehydration. In accordance with U.S. Pat. No. 2,674,602 to Schuster, N-alkyl lactams are obtained by reacting N-unsubstituted lactams with alcohols in the presence of catalysts for splitting off water. According to U.S. Pat. No. 2,843,600 to McKeever, alkyl beta-cyanopropionate is converted to 2-pyrrolidone by mixing a nickel hydrogenation catalyst with an inert organic liquid, supplying hydrogen under pressure to the mixture, heating the mixture to 150°-260° C. under agitation and adding a lower alkyl beta-cyanopropionate. The reaction mixture is maintained during the conversion of cyanopropionate to 2-pyrrolidone at 150°-300° C. and 200-5,000 psi or more. U.S. Pat. No. 3,080,377 to Liao describes the reductive aminolysis of succinic anhydride to produce 2-pyrrolidone. U.S. Pat. No. 3,095,423 to Copenhaven, et al. describes the hydrogenation of succinonitrile in the presence of water to provide 2-pyrrolidone and split out ammonia. The process of Prince U.S. Pat. No. 3,637,743 produces 2-pyrrolidone and N-substituted-2-pyrrolidones in one step by the carbonylation of allyl chloride in the presence of ammonia in a two phase solvent system, e.g., benzene and water. In U.S. Pat. No. 4,123,438 to Geurts, et al., a process for the preparation of 2-pyrrolidone is described in which succinonitrile is hydrogenated in the liquid phase in the presence of ammonia at 50°-200° C. and at a partial hydrogen pressure of 1-150 atmospheres and the resulting product is hydrolyzed. U.S. Pat. No. 4,181,662 to Sweeney describes the production of 2-pyrrolidone by hydrolyzing succinonitrile and hydrogenating the resulting hydrolysate in the presence of a heterogenous hydrogenation catalyst at 200°-300° C. and 100-10,000 psig. U.S. Pat. No. 4,183,866 to Kurkov discloses the production of 2-pyrrolidone by contacting 3-cyanopropanol with hydrogen in the presence of a prereduced copper chromite catalyst to yield a mixture of 3-cyanopropanol and gamma-butyrlactone and thereafter contacting said mixture with aqueous ammonia to convert the 3-cyanopropanol to 2-pyrrolidone.

SUMMARY OF THE INVENTION

It has now been discovered that 2-pyrrolidones can be readily and conveniently prepared by reacting methyl 4-oxobutyrate with ammonia and/or a primary amine in the presence of a catalytically effective amount of at least one hydrogenation catalyst.

The starting materials for this reaction are, in the case of ammonia, primary amine and hydrogen, relatively low cost commercially available reactants and in the case of methyl 4-oxobutyrate, can be prepared in useful quantities from relatively low cost acrolein, carbon monoxide and methanol by processes hereinafter more fully described.

DESCRIPTION OF THE PREFERRED EMBODIMENTS

The catalyzed reaction of methyl 4-oxobutyrate, ammonia and/or primary amine and hydrogen to provide a 2-pyrrolidone in accordance with the present invention can be considered to proceed overall as follows:

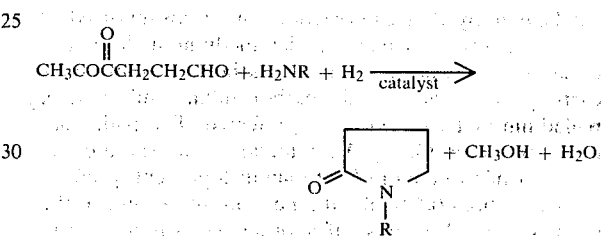

wherein R is hydrogen or a hydrocarbyl radical of up to 6 carbon atoms, optionally substituted with one or more up to half of the number of hydrogen atoms present in said radical with functional groups which do not significantly interfere with the reaction, e.g., hydroxyl, alkoxy, aryloxy, amino, etc. Thus, for example, when R is hydrogen, the resulting 2-pyrrolidone will be

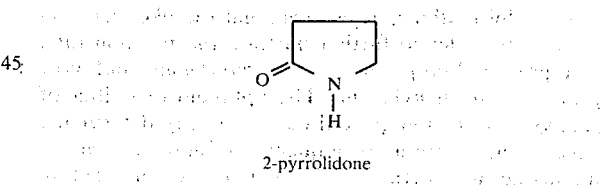

2-pyrrolidone

When R is methyl, the resulting product will be

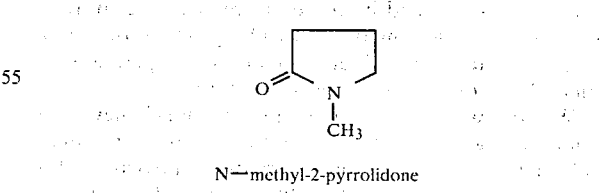

N—methyl-2-pyrrolidone and when R is hydroxyethyl, the substituted pyrrolidone will be

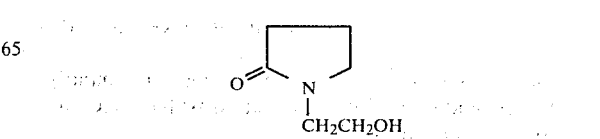

N—(beta-hydroxyethyl)-2-pyrrolidone

N-(Beta-hydroxyethyl)-2-pyrrolidone can be catalytically dehydrated employing known and conventional procedures to provide N-vinyl-2-pyrrolidone, the monomer used in the preparation of polyvinylpyrrolidone (PVP).

The starting compound, methyl 4-oxobutyrate (also named beta-carbomethoxypropionaldehyde), can be prepared by processes disclosed and claimed in U.S. patent application Ser. Nos. 264,925, filed May 18, 1981 and 274,847, filed June 18, 1981, the contents of which are incorporated by reference herein. In accordance with the process of Ser. No. 264,925, methyl 4-oxobutyrate and its acetals, i.e., methyl 4,4-dimethoxybutyrate and gamma methoxy-gamma butyrolactone, are obtained from the reaction of acrolein, carbon monoxide and methanol in the presence of a Group VIII metal catalyst promoted with hydrogen halide and optionally co-promoted with an arylarsine, arylbismuthine and/or arylstibine. Of the Group VIII metal catalysts which can be employed in said reaction, either unsupported or supported upon an inert carrier medium such as alumina, silica, titania, zirconia, carbon, diatomaceous earth, glass beads, ceramic, carborundum, and the like, palladium metal is especially preferred. The palladium metal or other Group VIII metal is incorporated in amounts of from about 0.1 to about 5 percent, preferably from about 0.5 to about 3 percent, by weight of the total supported catalyst. If another metal is present in the catalyst composition, it can be incorporated in an amount ranging from about 1 to about 500 percent, preferably from about 10 to about 200 percent, by weight based on the weight of the Group VIII metal. The metal catalyst is employed in the presence of a hydrogen halide, preferably hydrogen chloride. The hydrogen halide is believed to act as a promoter in the aforedescribed synthesis but is ultimately regenerated in situ. Optionally, a catalyst co-promoter such as arylarsine, arylbismuthine, arylstibine, and the like, can also be used in order to further increase the reaction rate. The preferred co-promoters are triarylarsine and most preferably triphenylarsine. The optimum quantities of catalyst and acid employed can be readily determined experimentally for a given quantity of acrolein, carbon monoxide and methanol and a given set of reaction conditions to achieve a desired reaction rate. Since the reaction of methyl 4-oxobutyrate with ammonia and/or a primary amine and hydrogen to provide a 2-pyrrolidone also produces methanol as a by-product, the latter can be recovered and utilized in the preparation of methyl 4-oxobutyrate as described herein.

Without wishing to be bound, acrolein is believed to undergo reaction with methanol and hydrogen halide (illustrated for hydrogen chloride) to provide beta-chloropropionaldehyde dimethyl acetal as follows:

$$CH_2=CHCHO + HCl + 2CH_3OH \longrightarrow ClCH_2CH_2CH(OCH_3)_2 + H_2O$$

Carbonylation of the acetal and subsequent methanolysis to provide methyl 4,4-dimethoxybutyrate are thought to proceed as follows:

$$ClCH_2CH_2CH(OCH_3)_2 + CO \xrightarrow[100°\,C.]{Pd/Support\ 1000-3000\ psi}$$

$$Cl\overset{O}{\underset{\|}{C}}CH_2CH_2CH(OCH_3)_2$$

$$Cl\overset{O}{\underset{\|}{C}}CH_2CH_2CH(OCH_3)_2 + CH_3OH \longrightarrow$$

$$CH_3O\overset{O}{\underset{\|}{C}}CH_2CH_2CH(OCH_3)_2 + HCl$$

In place of acrolein, an acetal of acrolein, e.g., $CH_2=CHCH(OCH_3)_2$, can be used. Accordingly, the term "acrolein" herein shall be understood as referring to acrolein or acrolein acetal.

The reaction may follow a different path via carbonylation of beta-chloropropionaldehyde formed by addition of HCl to acrolein as follows:

$$ClCH_2CH_2CHO + CO \xrightarrow{cat.} Cl\overset{O}{\underset{\|}{C}}CH_2CH_2CHO$$

Methanolysis of the acyl chloride provides methyl 4-oxobutyrate:

$$CH_3OH + Cl\overset{O}{\underset{\|}{C}}CH_2CH_2CHO \longrightarrow CH_3O\overset{O}{\underset{\|}{C}}CH_2CH_2CHO + HCl$$

The following example is illustrative of the aforedescribed process for preparing methyl 4-oxobutyrate.

EXAMPLE 1

A 300 ml Hastelloy reactor was provided with a stirrer, a thermocouple and a dip tube for sample withdrawal. Into the reactor was placed a mixture of 5 g 5% palladium supported on carbon and 3 g triphenylarsine. The reactor was purged with $N_2$ and charged with 100 ml solution containing 29.2 g acrolein (97% purity), 50.1 g methanol and 1.7 g anhydrous hydrogen chloride. The reactor was sealed and heated at 99°–106° C. under 2400–2900 psi of carbon monoxide with stirring. A sample was withdrawn after 30 minutes reaction time and analyzed by gas chromatography coupled with mass spectrometry. The analyses showed that the products were: methyl 4-oxobutyrate, methyl 4,4-dimethoxybutyrate and gamma-methoxy-gamma-butyrolactone. No branched isomers were detected in the reaction mixture. An aliquot of the above sample was analyzed for ester content (measure of carbonylation) by room temperature saponification after neutralization of free HCl at 0° C. The analysis indicated an acrolein conversion of 57.7% at 98.7% selectively to $C_4$ esters expressed as methyl 4-oxobutyrate. Analyses of an additional sample taken after one hour of reaction time indicated a conversion of 79% at 96.4% selectivity.

Compared to the optional use of a single ligand as disclosed in the foregoing process, the use of at least two ligands, one of which is an arsine ligand and the other of which is a non-arsine ligand, as described in Ser. No. 274,287 has been found to provide improved results. The non-arsine ligand is preferably present in a greater amount by weight than the arsine ligand, e.g., from about 1.1 to about 5 times the weight of the arsine ligand. The triaryl arsines are preferred, e.g., triphenylarsine and tri-p-tolyl arsine. The mole ratio of arsine to palladium can vary widely with mole ratios of from about 1:1 to about 4:1 providing good results in most instances. The non-arsine ligand can be selected from among any of the ligand forming compositions heretofore employed in carbonylation reactions and advantageously is selected to be an aryl phosphine, phosphite, stibine, bismuthine, and the like. Of the foregoing, the triarylphosphines are preferred and triphenylphosphine is especially preferred.

In the process of the present invention in which methyl 4-oxobutyrate is reacted with ammonia and/or a primary amine to provide 2-pyrrolidone(s), useful primary amine reactants include methylamine, ethylamine, propylamine, isopropylamine, n-butylamine, sec-butylamine, tert-butylamine, n-pentylamine, n-hexylamine, cyclohexylamine, 2-aminoethanol, 3-aminopropanol, and the like.

Any of the known and conventional hydrogenation catalysts, for example, palladium, platinum, nickel and ruthenium and/or alloys and compounds of these metals, optionally supported on an inert substrate such as alumina or carbon, can be used with good results. The amount of catalyst is not critical and can vary widely. At least a catalytic effective amount of catalyst should be used, of course. In general, an amount of catalyst which is effective to provide a reasonable reaction rate is sufficient depending on whether the reaction is continuous or batch. According to the exemplified reactions, it is generally sufficient in a batch reaction to provide from about 0.01% to about 1.0% by weight of catalyst (as metal) based on the total weight of the reactants.

Reaction temperatures and pressures and the duration of the reaction can similarly be varied over a wide range. It is generally preferred to operate within a temperature regime of from 80° to 200° C., preferably from about 90° to about 150° C. and a partial pressure of hydrogen of from about 250 to 2,000 psig, preferably from about 400 to about 1,500 psig, for a period of from about 15 minutes to about 24 hours, preferably from about 2 to about 10 hours. While stoichiometric amounts of methyl 4-oxobutyrate, ammonia and/or primary amine and hydrogen are entirely suitable, it is generally preferred to employ the ammonia/primary amine and hydrogen in at least slight molar excess to ensure total conversion of the methyl 4-oxobutyrate.

The following examples are further illustrative of the process of this invention.

EXAMPLE 2

A 1.04 g sample of methyl 4-oxobutyrate, prepared as in Example 1, was placed into a 70 ml pressure reactor provided with a glass liner. To the sample was added 10 g aqueous ammonia (29.4% NH$_3$), 10 g water and 0.2 g 5% ruthenium on carbon catalyst. The reactor was pressurized with 1,000 psig hydrogen, sealed and heated with shaking in an oven at 100° C. for four hours. After cooling to room temperature, the reactor was vented and its contents filtered. Analysis by gas chromatography showed that the filtrate contained 4.64 mmoles of 2-pyrrolidone as confirmed by mass spectrometry. The yield amounted to 51.6% based on the starting methyl 4-oxobutyrate.

EXAMPLE 3

Example 2 was repeated except that the catalyst was 0.2 g of 5% palladium on carbon. The yield of 2-pyrrolidone was 30%.

EXAMPLE 4

Example 2 was repeated except that the reactor charge contained 0.91 g methyl 4-oxobutyrate, 0.9 g anhydrous ammonia, 10 ml anhydrous ethanol and 0.2 g platinum oxide. The reactor was pressurized with hydrogen at 500 psig and heated at 100° for three hours. The analysis showed that 2-pyrrolidone was formed in 25.7% yield.

EXAMPLE 5

Example 2 was repeated except that 1.06 g methyl 4-oxobutyrate and 3.5 g anhydrous methylamine were used. The product was N-methyl-2-pyrrolidone as established by gas chromatography, mass spectrometry and nuclear magnetic reasonance. The yield was 45.4%.

EXAMPLE 6

Example 5 was repeated except that the 5% Ru/C catalyst was replaced with 0.2 g of 5% Pd/C. The yield of N-methyl-2-pyrrolidone was 33.8%.

EXAMPLE 7

A mixture of 1.1 g of methyl 4-oxobutyrate dissolved in 2 ml methanol, 4.05 g of 2-aminoethanol, and 0.2 g of 5% Ru/C was placed in a 70 ml glass-lined pressure reactor. The reactor was flushed and then pressurized with hydrogen to 1,000 psi, sealed and shaken in an air-oven at 100° C. for four hours. After cooling and venting of unreacted hydrogen, the mixture was filtered and analyzed by gas chromatography. The analysis disclosed complete conversion of methyl 4-oxobutyrate with formation of N-(beta-hydroxyethyl)-2-pyrrolidone as confirmed by gc-mass spectrometry.

What is claimed is:

1. A process for preparing an unsubstituted or N-substituted pyrrolidone having the structure:

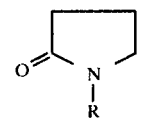

wherein R is H, a lower alkyl, or a lower hydroxyalkyl which comprises the step of reacting methyl 4-oxobutyrate with a compound having the formula

H$_2$NR wherein R is as previously defined, and hydrogen in the presence of a catalytically effective amount of a hydrogenation catalyst selected from the group consisting of palladium, platinum, nickel and ruthenium and alloys and compounds of the foregoing at a temperature of from 80° to 200° C. and a partial pressure of hydrogen of from 250 to 2,000 psig for from about 15 minutes to about 24 hours thus forming said unsubstituted or N-substituted pyrrolidone and methanol by-product.

2. The process of claim 1 wherein said catalyst is supported on an inert substrate.

3. The process of claim 1 wherein said catalyst is present at a level of from about 0.1% to about 1.0% of the total weight of the reactants.

4. The process of claim 1 carried out from about 90° to about 150° C. and from about 400 to about 1,500 psig partial pressure of hydrogen for from about 2 to about 10 hours.

5. The process of claim 1 wherein R is hydrogen.

6. The process of claim 1 wherein R is methyl.

7. The process of claim 1 wherein R is —CH$_2$CH$_2$OH.

* * * * *